US008609865B2

(12) United States Patent
Anzalone et al.

(10) Patent No.: US 8,609,865 B2
(45) Date of Patent: Dec. 17, 2013

(54) CRYSTALS AND PROCESS OF MAKING 5-({[2-AMINO-3-(4-CARBAMOYL-2,6-DIMETHYL-PHENYL)-PROPIONYL]-[1-(4-PHENYL-1H-IMIDAZOL-2-YL)-ETHYL]-AMINO}-METHYL)-2-METHOXY-BENZOIC ACID

(75) Inventors: Luigi Anzalone, West Chester, PA (US); Frank J. Villani, Perkasie, PA (US); Christopher A. Teleha, Fort Washington, PA (US); Penina Feibush, Ambler, PA (US); Barry Fegely, Quakertown, PA (US)

(73) Assignee: Furiex Pharmaceuticals, Inc., Morrisville, NC (US)

( * ) Notice: Subject to any disclaimer, the term of this patent is extended or adjusted under 35 U.S.C. 154(b) by 0 days.

(21) Appl. No.: 13/175,342

(22) Filed: Jul. 1, 2011

(65) Prior Publication Data

US 2011/0263868 A1    Oct. 27, 2011

Related U.S. Application Data

(62) Division of application No. 12/168,331, filed on Jul. 7, 2008.

(60) Provisional application No. 60/948,584, filed on Jul. 9, 2007.

(51) Int. Cl.
C07D 233/64    (2006.01)

(52) U.S. Cl.
USPC .................................................. 548/338.1

(58) Field of Classification Search
None
See application file for complete search history.

(56) References Cited

U.S. PATENT DOCUMENTS

| 7,629,488 | B2 * | 12/2009 | Cai et al. ........................ 562/406 |
| 7,741,356 | B2 * | 6/2010 | Breslin et al. .................. 514/396 |
| 7,786,158 | B2 * | 8/2010 | Breslin et al. .................. 514/396 |
| 7,994,206 | B2 | 8/2011 | Anzalone et al. |

FOREIGN PATENT DOCUMENTS

CN    1950342    4/2007

OTHER PUBLICATIONS

Caira "Crystalline Polymorphism of Organic Compounds," Topics in Current Chemistry, 1998, vol. 198, pp. 164-208.
Guillory, "Generation of Polymorphs, Hydrates, Solvates, and Amorphous Solids," Polymorphism in Pharmaceutical Solids, Chapter 5, Marcel Dekker, Inc., New York, 1999, 25 pages.
Knapman "Polymorphic predictions: Understanding the nature of crystalline compounds can be critical in drug development and manufacture," Modern Drug Discovery, Mar. 2000, 3 pages.
Swanepoel et al. "Quality evaluation of generic drugs by dissolution test: changing the USP dissolution medium to distinguish between active and non-active mebendazole polymorphs," European Journal of Pharmaceutics and Biopharmaceutics, 2003, vol. 55, pp. 345-349.
English Translation of Official Action for China Patent Application No. 200880024059.7, dated Jul. 5, 2011 10 pages.
Official Action with English translation for China Patent Application No. 200880024059.7, dated Jul. 13, 2012 7 pages.
Official Action with English translation for Eurasian Patent Application No. 201070116/28, dated Jul. 6, 2011 4 pages.
Official Action with English translation for Eurasian Patent Application No. 201070116/28, dated Mar. 30, 2012 4 pages.
Official Action for European Patent Application No. 08781434.9, dated Jun. 15, 2011 3 pages.
Official Action for European Patent Application No. 08781434.9, dated Dec. 8, 2011 3 pages.
Pre-Grant Opposition for India Patent Application No. 58/KOLNP/2010, dated Nov. 13, 2010 26 pages.
Official Action with English translation for Ukraine Patent Application No. 201001286, dated Feb. 10, 2012 8 pages.
Opposition with English Translation for Ecuador Patent Application No. 10-9863, dated May 28, 2012 21 pages.
Examination Report for Singapore Patent Application No. 201000095-8, dated Aug. 14, 2012 7 pages.
"Handbook of Pharmaceutical Salts: Properties, Selection, and Use," Stahl et al. (Eds.), Wiley-VCH, 2008, pp. 16-17.
"Pharmaceutical Manufacturing Handbook: Production and Processes," GAD editor, Wiley-Interscience, 2008, pp. 952-954.
"Remington: Farmacia 2" Editorial Medica Panamericana, Argentina, 1992, pp. 1912-1920.
International Search Report for International (PCT) Patent Application No. PCT/US2008/069318, Mailed Jan. 29, 2009.
International Preliminary Report on Patentability for International (PCT) Patent Application No. PCT/US2008/069318, dated Jan. 12, 2010.
Official Action for Australia Patent Application No. 2008275270, dated Oct. 23, 2012.
Official Action for Colombia Patent Application No. 10.000.935, dated Sep. 2012.
English Translation of Official Action for Philippines Patent Application No. 1/2010/500060, dated Oct. 25, 2012.
Official Action with English Translation for Vietnam Patent Application No. 1-2009-02869, dated Jun. 21, 2012.
Official Action for U.S. Appl. No. 12/168,331, mailed May 14, 2010 Restriction Requirement.
Official Action for U.S. Appl. No. 12/168,331, mailed Jul. 12, 2010.
Official Action for U.S. Appl. No. 12/168,331, mailed Dec. 29, 2010.

(Continued)

Primary Examiner — Sun Jae Loewe
(74) Attorney, Agent, or Firm — Sheridan Ross P.C.

(57) ABSTRACT

The present invention relates to a novel crystals of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid and methods of making the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid.

7 Claims, 6 Drawing Sheets

(56) References Cited

OTHER PUBLICATIONS

Notice of Allowance for U.S. Appl. No. 12/168,331, mailed Apr. 6, 2011.
Chawla et al. "Challenges in Polymorphism of Pharmaceuticals," CRIPS, vol. 5, No. 1, Jan.-Mar. 2004, 4 pages.
Newman et al. "Solid-state analysis of the active pharmaceutical ingredient in drug products," DDT, Oct. 2003, vol. 8, No. 19, pp. 898-905.
English Translation of Official Action for Japan Patent Application No. 2010-516175, dated May 28, 2013 4 pages.
Official Action for Australia Patent Application No. 2008275270, mailed Mar. 28, 2013 3 pages.
Official Action with English Translation for China Patent Application No. 200880024059.7, dated Apr. 11, 2013 13 pages.
English Translation of Official Action for Israel Patent Application No. 203081, dated Apr. 25, 2013 3 pages.
Official Action for Malaysia Patent Application No. PI 2010000053, mailed Apr. 15, 2013 3 pages.
Official Action with English Translation for Ukraine Patent Application No. 201001286, dated Feb. 25, 2013 6 pages.
"Crystallization Technology Handbook," Marcel Dekker, Inc., ed. A. Mersmann, 2001, second edition, pp. 13, 516, 544-550.
"Springer Handbook of Crystal Growth," Springer, editors Dhanaraj et al., 2010, pp. 75-76, 566.
English Translation of Official Action for Colombia Patent Application No. 10-000935, 10 pages.
English Summary of Official Action for Egypt Patent Application No. 33/2010, Sep. 2013 2 pages.

\* cited by examiner

Top line is Form β crystal
Bottom line is Form α crystal

CRYSTALS AND PROCESS OF MAKING 5-({[2-AMINO-3-(4-CARBAMOYL-2,6-DIMETHYL-PHENYL)-PROPIONYL]-[1-(4-PHENYL-1H-IMIDAZOL-2-YL)-ETHYL]-AMINO}-METHYL)-2-METHOXY-BENZOIC ACID

CROSS REFERENCE TO RELATED APPLICATION

This application is a divisional of U.S. application Ser. No. 12/168,331, filed Jul. 7, 2008, which claims priority to U.S. Application No. 60/948,584, filed on Jul. 9, 2007, both of which are incorporated herein by reference in their entireties.

FIELD OF THE INVENTION

The present invention relates to novel crystals of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid and methods of making the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid.

BACKGROUND OF THE INVENTION

Delivering an API to a patient requires more than just identifying a molecule and its use. An API must be formulated for delivery to a patient and this formulation (in addition to the API activity) is evaluated by regulatory agencies such as the US Food and Drug Administration (FDA) and the European Medicines Agency (EMEA). The FDA evaluates the formulation for, among other properties, delivery properties, stability, consistency, and manufacturing controls. An important factor in determining the properties of a particular formulation is the form of the API. APIs have been known to exist as amorphous forms, crystalline forms, polymorphs, hydrates and solvates. The forms for every API are different. While one particular API may be known to exist as a polymorph or a solvate, another API may be known to only exist in amorphous form. This form diversity is important because each different polymorph, solvate, hydrate or amorphous form may have different properties such as stability, solubility, and hygroscopicity.

Some forms of an API can be formulated into an FDA approvable formulation, while other forms lack the required properties to meet the high regulatory standards of the FDA. Even if a particular API can exist in more than one form suitable for formulation, different properties of an API form can affect the manufacturing process, shelf stability, route of administration, bioavailability and other important product characteristics. For example, the ability to improve or modulate stability or hygroscopicity can decrease manufacturing costs by reducing the need for humidity controlled chambers or reducing the need to package an API in humidity resistant packaging. In addition these same changes can increase product shelf stability thereby improving product distribution possibilities and affecting cost. In another example, one form of an API may have greater bioavailability than another form. Choosing the higher bioavailability form allows for a lower drug dose to be administered to a patient.

Further, changes to the process of making an API can result in less processing steps, higher purity and lower cost. Such advantages are important to the pharmaceutical industry.

5-({[2-Amino-3-(4-carbamoyl-2,6-dimethyl-phenyl)-propionyl]-[1-(4-phenyl-1 h-imidazol-2-yl)-ethyl]-amino}-methyl)-2-methoxy-benzoic acid is an opoid receptor modulator (mu receptor agonist and delta receptor antagonist) and may be useful for treating irritable bowel syndrome, pain or other opioid receptor disorders. 5-({[2-Amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid and methods of making this molecule are disclosed in US application 2005/02033143. Example 9 of US application 2005/02033143 makes the hydrochloride salt of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. Applicants have discovered a process of making the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid and two novel crystals of this zwitterion. In Applicant's hands, these novel crystals provide improved properties and can be purified at higher purity. Applicant's new process results in improved and less costly process manufacturing conditions than the procedure disclosed in US application 2005/02033143.

SUMMARY OF THE INVENTION

The present invention relates to a Form α and a Form β crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. The invention also provides for methods of making the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. The invention also provides pharmaceutical compositions comprising these novel crystals. Compositions and methods of the invention are useful in the treatment or prevention of a variety of diseases including, among others, irritable bowel syndrome.

DETAILED DESCRIPTION

Figure 1:
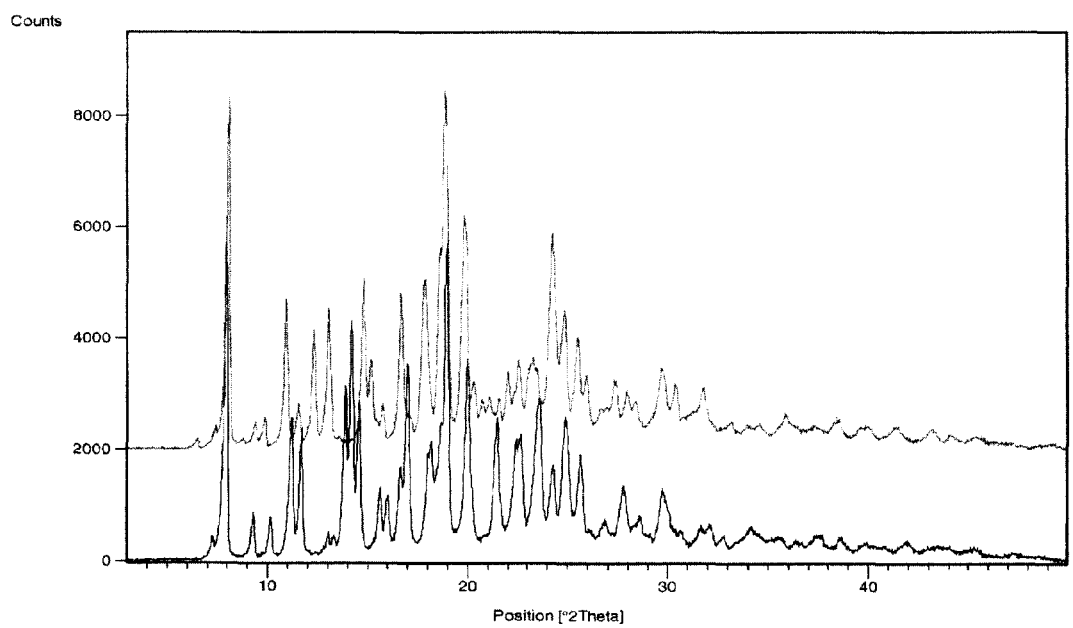
FIG. 1 illustrates powder X-ray diffraction (PXRD) measurements of a representative Form α crystal.

The present invention is directed to a novel Form α crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid useful for treating irritable bowel syndrome.

In a first embodiment, the present invention comprises a Form α crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. In one aspect of this invention, a Form α crystal is characterized by a powder X-ray diffraction pattern having powder X-ray diffraction peaks at about 14.0, 14.3, and 14.7 degrees 2-theta. In a further aspect of this invention, a Form α crystal is characterized by a powder X-ray diffraction pattern having powder X-ray diffraction peaks at about 10.2, 11.3, 14.0, 14.3, and 14.7 degrees 2-theta. In a still further aspect of this invention, a Form α crystal is characterized by a powder X-ray diffraction pattern having powder X-ray diffraction peaks at about 10.2, 11.3, 11.8, 14.0, 14.3, 14.7, 16.1, and 18.3 degrees 2-theta. In another aspect of this invention, a Form α crystal is characterized by a powder X-ray diffraction pattern having powder X-ray diffraction peaks substantially as shown in Table 1. In another embodiment, a Form α crystal is characterized by a powder X-ray diffraction pattern that is substantially similar to the powder X-ray diffraction pattern of FIG. 1. In a further aspect of this invention, a Form α crystal is characterized by a thermal gravimetric analysis (TGA) substantially similar to the TGA in FIG. 2. In a further aspect of this invention, a Form α crystal is characterized by a differential scanning calorimetry (DSC) measurement substantially similar to the DSC in FIG. 3. In one embodiment of this invention, a Form α crystal is substantially pure.

In another embodiment, the present invention comprises a method of treating a mammal suffering from an opioid receptor disorder such as irritable bowel syndrome, comprising administering to said mammal an effective amount of a Form α crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. In another embodiment, said mammal is a human.

TABLE 1

| Position [°2θ] |
| --- |
| 8.0 |
| 9.4 |
| 10.2 |
| 11.3 |
| 11.8 |
| 14.0 |
| 14.3 |
| 14.7 |
| 15.7 |
| 16.1 |
| 16.7 |
| 17.1 |
| 18.1 |
| 18.3 |
| 18.7 |
| 19.1 |
| 20.1 |
| 21.5 |
| 22.5 |
| 22.7 |
| 23.7 |
| 24.4 |
| 25.0 |
| 25.7 |
| 26.9 |
| 27.8 |
| 28.7 |
| 29.8 |

The present invention is also directed to a novel Form β crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid which may be useful for treating irritable bowel syndrome, pain or other opioid receptor disorders.

In a first embodiment, the present invention comprises a Form β crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. In one aspect of this invention, a Form β crystal is characterized by a powder X-ray diffraction pattern having powder X-ray diffraction peaks at about 11.0, 12.4, and 15.2 degrees 2-theta. In a further aspect of this invention, a Form β crystal is characterized by a powder X-ray diffraction pattern having powder X-ray diffraction peaks at about 11.0, 12.4, 14.9, 15.2, and 22.1 degrees 2-theta. In a still further aspect of this invention, a Form 0 crystal is characterized by a powder X-ray diffraction pattern having powder X-ray diffraction peaks at about 11.0, 12.4, 14.9, 15.2, 22.1, 25.6, 27.4, and 30.4 degrees 2-theta. In another aspect of this invention, a Form β crystal is characterized by a powder X-ray diffraction pattern having powder X-ray diffraction peaks substantially as shown in Table 2. In another embodiment, a Form β crystal is characterized by a powder X-ray diffraction pattern that is substantially similar to the powder X-ray diffraction pattern of FIG. 1. In a further aspect of this invention, a Form β crystal is characterized by a thermal gravimetric analysis (TGA) substantially similar to the TGA in FIG. 4. In a further aspect of this invention, a Form β crystal is characterized by a differential scanning calorimetry (DSC) measurement substantially similar to the DSC in FIG. 5. In one embodiment of this invention, a Form β crystal is substantially pure.

In another embodiment, the present invention comprises a method of treating a mammal suffering from an opioid receptor disorder such as irritable bowel syndrome, comprising administering to said mammal an effective amount of a Form β crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. In another embodiment, said mammal is a human.

TABLE 2

| Position [°2θ] |
| --- |
| 8.1 |
| 11.0 |
| 11.6 |
| 12.4 |
| 13.1 |
| 14.9 |
| 15.2 |
| 15.5 |
| 15.8 |
| 16.8 |
| 17.1 |
| 17.9 |
| 18.7 |
| 19.0 |
| 19.9 |
| 20.4 |
| 20.8 |
| 21.2 |
| 21.6 |
| 22.1 |
| 22.6 |
| 23.3 |
| 23.5 |
| 24.3 |
| 24.9 |
| 25.6 |
| 26.0 |
| 26.7 |
| 27.0 |
| 27.4 |
| 27.5 |
| 28.0 |
| 28.5 |
| 29.8 |
| 30.4 |
| 31.8 |
| 38.6 |

Pharmaceutical dosage forms of crystals of 5-({[2-amino-3-(4-carbamoyl-2,6-dimethyl-phenyl)-propionyl]-[1-(4- phenyl-1 h-imidazol-2-yl)-ethyl]-amino}-methyl)-2-methoxy-benzoic acid can be administered in several ways including, but not limited to, oral administration. Oral pharmaceutical compositions and dosage forms are exemplary dosage forms. Optionally, the oral dosage form is a solid dosage form, such as a tablet, a caplet, a hard gelatin capsule, a starch capsule, a hydroxypropyl methylcellulose (HPMC) capsule, or a soft elastic gelatin capsule. Liquid dosage forms may also be provided by the present invention, including such non-limiting examples as a suspension, a solution, syrup, or an emulsion. In another embodiment, the present invention includes the preparation of a medicament comprising a crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. A Form β crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid can be administered by controlled- or delayed-release means.

Like the amounts and types of excipients, the amounts and specific type of active ingredient in a dosage form may differ depending on factors such as, but not limited to, the route by which it is to be administered to mammals. However, typical dosage forms of the invention comprise a Form β crystal of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid, in an amount of from about 0.10 mg to about 1.00 g, from about 0.2 mg to about 500.0 mg, or from about 1.0 mg to about 250.0 mg. Non-limiting examples include 0.2 mg, 0.50 mg, 0.75 mg, 1.0 mg, 1.2 mg, 1.5 mg, 2.0 mg, 3.0 mg, 5.0 mg, 7.0 mg, 10.0 mg, 25.0 mg, 50.0 mg, 100.0 mg, 250.0 mg, and 500.0 mg dosages. The dosages, however, may be varied depending upon the requirement of the patients, the severity of the condition being treated and the compound being employed. The use of either daily administration or post-periodic dosing may be employed.

The crystals of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid of the present invention may also be used to prepare pharmaceutical dosage forms other than the oral dosage forms described above, such as topical dosage forms, parenteral dosage forms, transdermal dosage forms, and mucosal dosage forms. For example, such forms include creams, lotions, solutions, suspensions, emulsions, ointments, powders, patches, suppositories, and the like.

The crystals of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid of the present invention can be characterized by the TGA or DSC data, or by any one, any two, any three, any four, any five, any six, any seven, any eight, any nine, or any ten PXRD 2-theta angle peaks, or by any combination of the data acquired from the analytical techniques described above which distinctly identify the particular crystal.

The present invention is also directed to a method of isolating and preparing the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. In one embodiment, a method of preparing the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid comprises the steps of: combining a strong ionizable acid with 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to prepare a salt of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid; and washing said salt of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid an inorganic base to obtain the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid. In another embodiment, the invention further comprises the step of washing said zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid with water. In one aspect of the invention the inorganic base is selected from sodium hydroxide, potassium hydroxide, sodium carbonate, sodium acetate, sodium phosphate. In another aspect of the invention the inorganic base is sodium hydroxide. In a further aspect of the invention, the ionizable acid is selected from hydrochloric acid, trifluoroacetic acid, sulphuric acid, formic acid, and phosphoric acid. In another aspect of the invention, said ionizable acid is hydrochloric acid.

In one embodiment, a method of preparing the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid comprises the steps of: combining hydrochloric acid with 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to prepare the hydrochloride salt of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid; washing said salt of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid with sodium hydroxide; and washing said zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid with water.

In another embodiment, the invention comprises subjecting the zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid resulting from a process of this invention to recrystallization. In a further embodiment, such recrystallization is done at a relative humidity of between 0-40%. In a still further embodiment, such recrystallization is done at a relative humidity of greater than 60%.

In one embodiment, the invention comprises crystalline zwitterion of 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid prepared by the process of this invention. In a further embodiment, the crystalline zwitterion made by a process of this invention is a Form α crystal. In a still further embodiment, the crystalline zwitterion made by a process of this invention is a Form β crystal.

In one embodiment, a crystal of this invention has improved stability.

Although the invention has been described with respect to various embodiments, it should be realized this invention is also capable of a wide variety of further and other embodiments within the spirit and scope of the appended claims.

The Crystals of the Present Invention were Analyzed Using the Following Methods

Differential Scanning Calorimetry

Both crystals were analyzed using the Perkin-Elmer DSC-7 from ca. 25° C. to 250° C. at a heating rate of 10° C./min.

Powder X-Ray Diffraction

Analysis was performed using a Philips X'Pert Pro MPD diffractometer. Each sample was backloaded and analyzed in a 16 mm sample holder. Using the X-Celerator detector, each sample was scanned from 3 to 50° 2θ at a step size of 0.0165° 2θ and a time per step of 10.16 seconds. The effective scan speed was 0.2067°/s. Instrument voltage and current settings of 45 kV and 40 mA were employed.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, or by about +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.2 degrees 2-theta. Unless otherwise noted, all diffractograms are obtained at about room temperature (about 24 degrees C. to about 25 degrees C.).

Thermal Gravimetric Analysis

Both crystals were analyzed using the Perkin-Elmer TGA-7 from ca. 25° C. to either 200 or 250° C. at a heating rate of 10° C./min.

The following specific examples illustrate the present invention in more detail. They are, however, not intended to limit its scope in any manner.

EXAMPLES

Example 1

Preparation of the zwitterion of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid A 1 L three-necked round-bottomed flask equipped with a mechanical stirrer, addition funnel and a thermocouple was charged without agitation. 34.2 g of 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxy-benzoic acid (see Example 9 of US 2005/0203143), 340 ml of acetone, and 17 ml of 204 mmolar concentrated HCl were combined in the flask. The stirring was started and the resulting slurry formed a clear solution. This solution was heated to 45° C. under vigorous stirring and aged at this temperature for a period of two hours. After the completion, the reaction mass was cooled to ambient temperature and the supernatant was removed by suction. The vessel along with the residue was rinsed with 20 ml of acetone and then removed as previously. 170 ml of water was added and the reaction mass and was aged under stirring until a homogenous solution resulted. This solution was then added over a period of ~½ hr to a solution of 90 ml of 1N NaOH and water. The pH was adjusted to 6.5-7.0 accordingly. The resulting slurry was aged for about 2 hrs at ambient temperature, cooled to 10-15° C., aged at that temperature for about 1 hr, and then filtered. The solid was washed with 10 ml water, air-dried for a period of 4 to 5 hrs, and then placed in a vacuum oven at 50-55° C. until the water content was less than 3%.

Example 2

Preparation of the Form α Crystal

Figure 2:
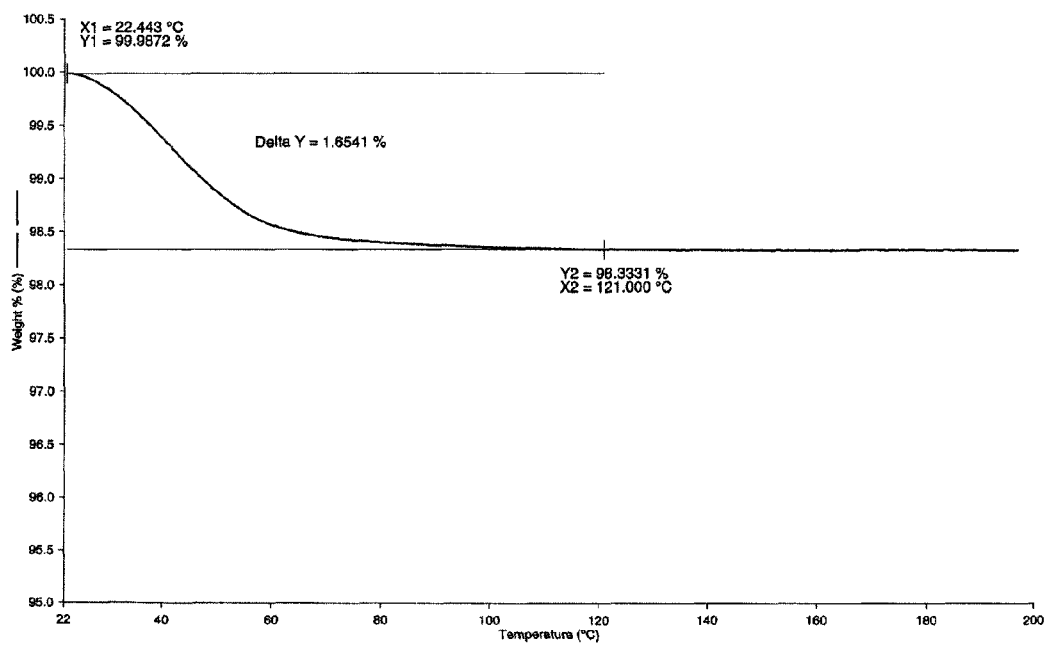
FIG. 2 illustrates a thermal gravimetric analysis (TGA) measurement of a representative Form α crystal.
Figure 3:
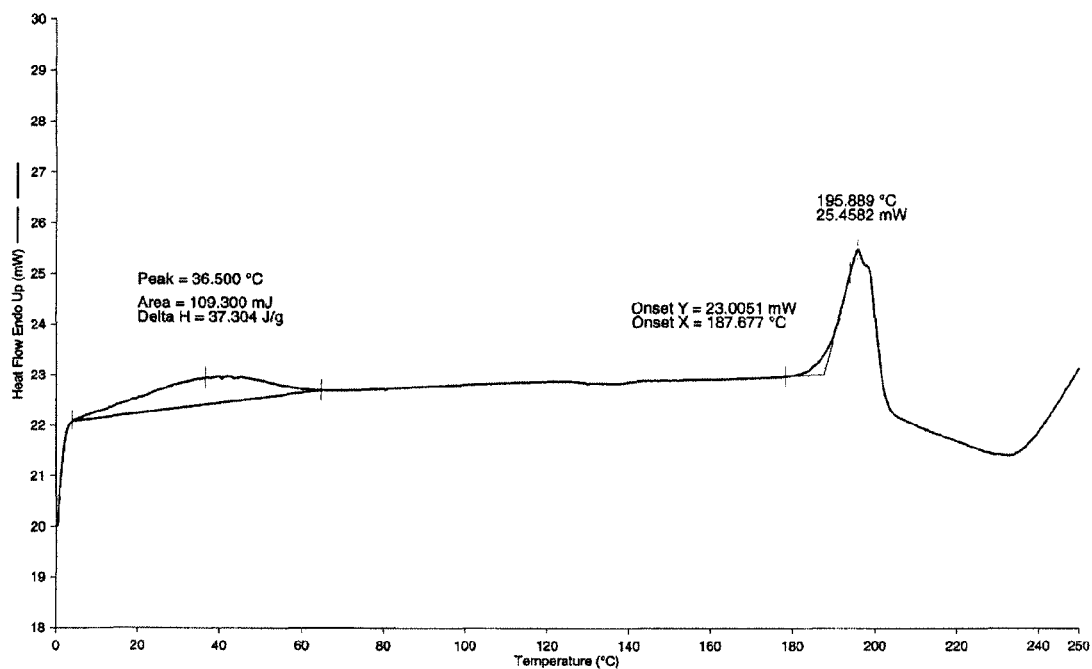
FIG. 3 illustrates a differential scanning calorimetry (DSC) measurement of a representative Form α crystal.

The Form α crystal can be prepared by storing the zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid at 0-25% relative humidity for 3 days. Representative PXRD, TGA, and DSC data are shown in FIGS. 1-3 respectively.

Example 3

Preparation of the Form β crystal

Figure 4:
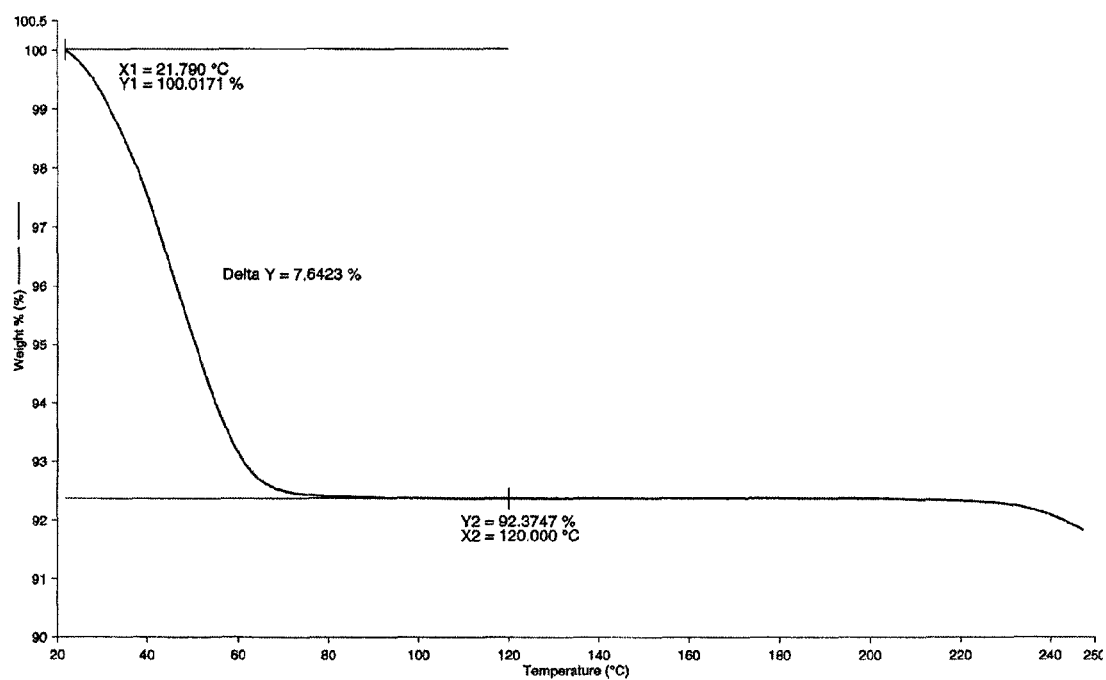
FIG. 4 illustrates a thermal gravimetric analysis (TGA) measurement of a representative Form β crystal.
Figure 5:
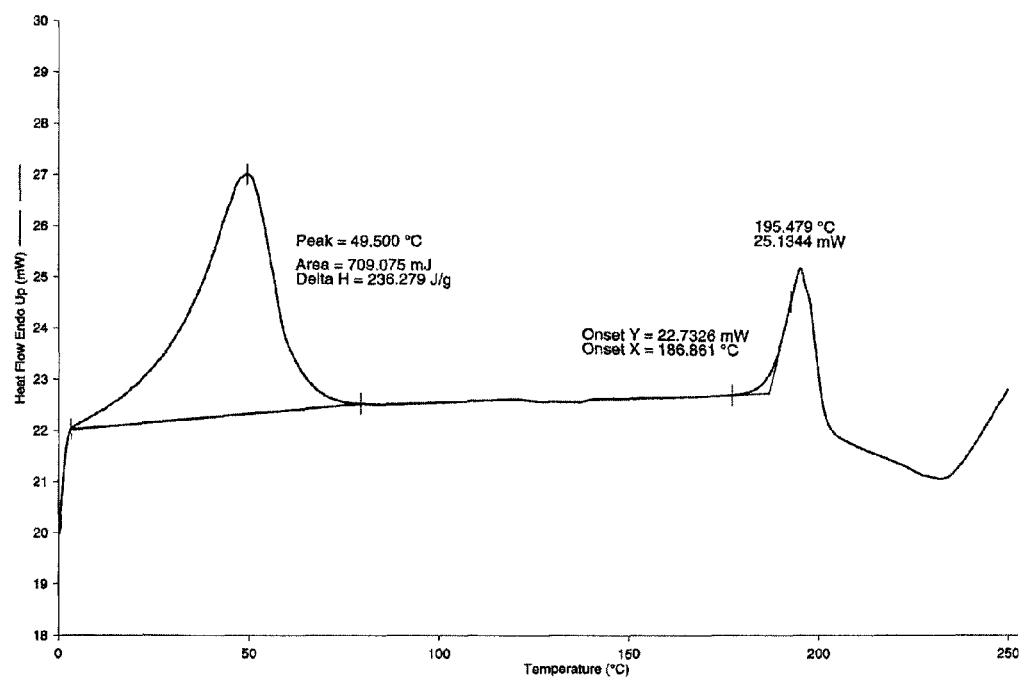
FIG. 5 illustrates a differential scanning calorimetry (DSC) measurement of a representative Form β crystal.
Figure 6:
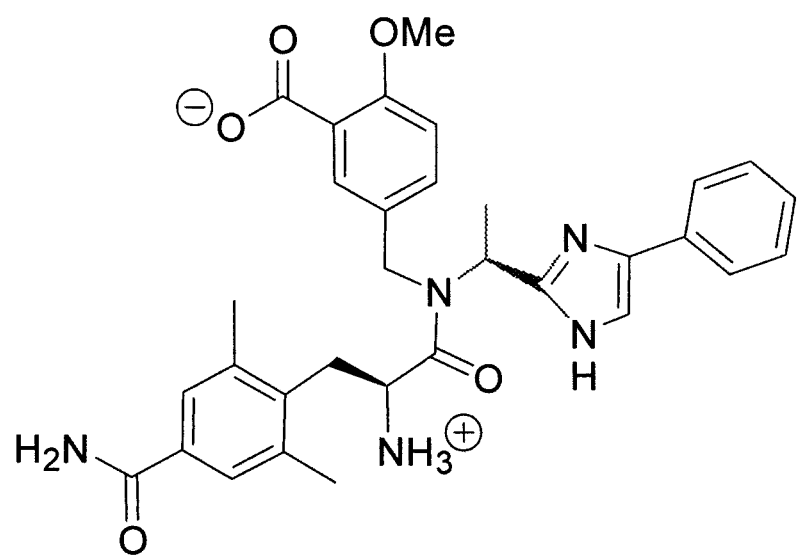
FIG. 6 is the molecular structure of the zwitterion 5-({[2-amino-3-(4-carbamoyl-2,6-dimethyl-phenyl)-propionyl]-[1-(4-phenyl-1h-imidazol-2-yl)-ethyl]-amino}-methyl)-2-methoxy-benzoic acid.

The Form β crystal can be prepared by storing the zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid at greater than 60% relative humidity for 3 days. Representative PXRD, TGA, and DSC data are shown in FIGS. 1, 4, and 5 respectively.

What is claimed:

1. A method of preparing a crystalline zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid comprising the steps of:
    combining a strong ionizable acid with 5-({[2-tert-butoxycarbonylamino-3-(4-carbamoyl-2,6-dimethyl-phenyl)-propionyl]-[1-(4-phenyl-1 H-imidazol-2-yl)-ethyl]-amino}-methyl)-2-methoxy-benzoic acid to prepare a salt of 5-({[2-amino-3-(4-carbamoyl-2,6-dimethyl-phenyl)-propionyl]-[1-(4-phenyl-1 H-imidazol-2-yl)-ethyl]-amino}-methyl)-2-methoxy-benzoic acid;
    washing said salt of 5-({[2-amino-3-(4-carbamoyl-2,6-dimethyl-phenyl)-propionyl]-[1-(4-phenyl-1H-imidazol-2-yl)-ethyl]-amino }-methyl)-2-methoxy-benzoic acid with an inorganic base to obtain the zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid; and
    crystallizing the zwitterion wherein the crystallizing comprises storing the zwitterion at a relative humidity of between about 0 to about 40% or at greater than about 60%.

2. The method of claim 1, further comprising the step of washing said zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with water.

3. The method of claim 1, wherein said inorganic base is sodium hydroxide.

4. The method of claim 1, wherein said ionizable acid is hydrochloric acid and wherein said salt is the hydrochloride salt of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid.

5. A method of preparing a crystalline zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid comprising the steps of:

combining hydrochloric acid with 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxybenzoic acid to prepare the hydrochloride salt of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid;

washing said salt of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with sodium hydroxide to obtain the zwitterion of 5-({[2-amino-3-(4-carbamoyl-2,6-dimethyl-phenyl)-propionyl]-[1-(4phenyl-1H-imidazol-2-yl)-ethyl]-amino}-methyl)-2-methoxy-benzoic acid;

washing said zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with water; and crystallizing the zwitterion wherein the crystallizing comprises storing the zwitterion at a relative humidity of between about 0 to about 40% or at greater than about 60%.

6. The method of claim 1, wherein the crystalline zwitterion comprises a Form α crystal and crystallizing comprises storing the zwitterion at a relative humidity of between about 0 to about 40%.

7. The method of claim 1, wherein the crystalline zwitterion comprises a Form β crystal and crystallizing comprises storing the zwitterion at a relative humidity of greater than about 60%.

* * * * *